US010527582B2

(12) United States Patent
Lauraeus et al.

(10) Patent No.: US 10,527,582 B2
(45) Date of Patent: Jan. 7, 2020

(54) USE OF STATIONARY PHASE COMPRISING FIBRIL CELLULOSE IN SEPARATION METHODS

(71) Applicant: UPM-KYMMENE CORPORATION, Helsinki (FI)

(72) Inventors: Marko Lauraeus, Vihti (FI); Antti Laukkanen, Helsinki (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 462 days.

(21) Appl. No.: 14/368,121

(22) PCT Filed: Dec. 18, 2012

(86) PCT No.: PCT/FI2012/051263
§ 371 (c)(1),
(2) Date: Jun. 23, 2014

(87) PCT Pub. No.: WO2013/093196
PCT Pub. Date: Jun. 27, 2013

(65) Prior Publication Data
US 2014/0374254 A1    Dec. 25, 2014

(30) Foreign Application Priority Data

Dec. 22, 2011   (FI) .................................... 20116317

(51) Int. Cl.
| G01N 27/447 | (2006.01) |
| B01D 15/38  | (2006.01) |
| B01D 15/36  | (2006.01) |
| B01D 15/20  | (2006.01) |
| B01D 15/34  | (2006.01) |

(52) U.S. Cl.
CPC ....... *G01N 27/44747* (2013.01); *B01D 15/20* (2013.01); *B01D 15/34* (2013.01); *B01D 15/361* (2013.01); *B01D 15/3804* (2013.01)

(58) Field of Classification Search
CPC .... G01N 27/4474; B01D 15/20; B01D 15/34; B01D 15/361; B01D 15/3804; B01J 20/28047; B01J 20/285; B01J 20/291
USPC ........................................................ 204/469
See application file for complete search history.

(56) References Cited

U.S. PATENT DOCUMENTS

2009/0308811 A1    12/2009  Tepper et al.
2010/0236932 A1*    9/2010  Alpenfels ........ G01N 27/44747
                                                    204/616

FOREIGN PATENT DOCUMENTS

| JP | S6383144 A | 4/1988 |
| JP | 4295759 A | 10/1992 |
| JP | H04295759 | * 10/1992 |
| JP | H04295759 A | 10/1992 |
| JP | 7193 A | 1/1995 |
| JP | H07232060 A | 9/1995 |

(Continued)

OTHER PUBLICATIONS

Tabuchi, M. et al. (2005). "Design for DNA Separation Medium Using Bacterial Cellulose Fibrils." Anal. Chem. 77:7090-7093.*

(Continued)

*Primary Examiner* — Jill A Warden
*Assistant Examiner* — Jacqueline Brazin
(74) *Attorney, Agent, or Firm* — Nixon Peabody LLP (57) ABSTRACT

Separation methods based on electrophoresis or chromatography that use a stationary phase including fibril cellulose.

12 Claims, 3 Drawing Sheets

(56) References Cited

FOREIGN PATENT DOCUMENTS

| | | | |
|---|---|---|---|
| JP | 2009014377 | * | 1/2009 |
| JP | 2009014377 A | | 1/2009 |
| JP | 2010236975 A | | 10/2010 |
| WO | WO2013/117823 | * | 8/2013 |

OTHER PUBLICATIONS

Paakko, M. et al. (2007). "Enzymatic Hydrolysis Combined with Mechanical Shearing and High-Pressure Homogenization for Nanoscale Cellulose Fibrils and Strong Gels." Biomacromolecules. 8:1934-1941.*

Cervin et al., "Ultra porous nanocellulose aerogels as separation medium for mixtures of oil/water liquids", Cellulose, 2012, vol. 19, pp. 401-410.

Tabuchi et al., "Design for DNA Separation Medium Using Bacterial Cellulose Fibrils", Analytical Chemistry, 2005, vol. 77, pp. 7090-7093.

Database WPI, Week 199248, Thompson Scientific, 1992, XP002694145, abstract.

Database WPI, Week 201171, Thompson Scientific, 2011, XP002694146, abstract.

Database WPI, Week 198904, Thompson Scientific, 1988, XP002694147, abstract.

Database WPI, Week 200550, Thompson Scientific, 2005, XP002694148, abstract.

Finnish Search Report, dated Oct. 18, 2012, from corresponding FI application.

International Search Report, dated Apr. 2, 2013, from corresponding PCT application.

Tabuchi et al., "Design for DNA separation medium using bacterial cellulose fibrils", Anal Chem, 77(21):7090-3 (2005).

Japanese Notice of Reasons of Refusal received in JP Application No. 2014-548118. dated Nov. 1, 2016. English Translation. 7pp.

* cited by examiner

USE OF STATIONARY PHASE COMPRISING FIBRIL CELLULOSE IN SEPARATION METHODS

FIELD OF THE INVENTION

The invention deals with new applications of fibril cellulose. The invention relates to a method of using a stationary phase comprising fibril cellulose in separation methods. Particularly the invention relates to the use and method of using a stationary phase comprising fibril cellulose in separation methods based on electrophoresis or chromatography.

BACKGROUND

One of the most common problems in chemical and biochemical research is to separate components from each other, for example larger molecules from smaller ones, macromolecules in cell extracts and the like. Methods for separating components of a mixture exploit differences in properties of the components, such as in size, electrical charge, solubility in different solvents, affinity and hydrophobic interactions.

Exclusion chromatography refers to a technique in which the separation is based mainly on exclusion effects, such as differences in molecular size and/or shape and/or in charge, and it includes size-exclusion chromatography (SEC).

Size-exclusion chromatography (SEC), also called gel-filtration chromatography (GFC) or gel-permeation chromatography (GPC) uses porous particles to separate molecules of different sizes when the stationary phase is a swollen gel. It is usually applied to large molecules or macromolecular complexes such as proteins and industrial polymers. Typically, when an aqueous solution is used to transport the sample through the column, the technique is known as GFC, versus the name GPC when an organic solvent is used as a mobile phase. SEC is also used for polymer characterization.

The main application of gel-filtration chromatography is the fractionation of proteins and other water-soluble polymers, while gel permeation chromatography is used to analyze the molecular weight distribution of organic-soluble polymers.

SEC is used for the purification and analysis of synthetic and biological polymers, such as proteins, polysaccharides and nucleic acids. Biologists and biochemists typically use a gel medium, usually polyacrylamide or agarose and filter under low pressure. Polymer chemists use either a silica or cross-linked polystyrene medium under a higher pressure. These media are known as the stationary phase.

SEC can be used to determine molecular weights and molecular weight distributions of polymers and to give polymer chemists information on the polydispersity of the sample. The preparative SEC can be used for polymer fractionation on an analytical scale.

Molecules that are smaller than the pore size of the stationary phase particles can enter the particles and therefore have a longer path and longer transit time than larger molecules that cannot enter the particles. SEC is a chromatographic technique that employs specialized columns to separate natural and synthetic polymers, biopolymers, proteins and nanoparticles on the basis of size. A column is filled with semi-solid beads of a polymeric gel that will admit ions and small molecules into their interior but not large ones. When a mixture of molecules and ions dissolved in a solvent is applied to the top of the column, the smaller molecules (and ions) are distributed through a larger volume of solvent than is available to the large molecules. Consequently, the large molecules move more rapidly through the column, and in this way the mixture can be separated (fractionated) into its components. The porosity of the gel can be adjusted to exclude all molecules above a certain size.

Molecules larger than the pore size cannot enter the pores and elute together as the first peak in the chromatogram. This condition is called total exclusion. Molecules that can enter the pores will have an average residence time in the particles that depends on the molecules size and shape. Different molecules therefore have different total transit times through the column. This portion of a chromatogram is called the selective permeation region. Molecules that are smaller than the pore size can enter all pores, and have the longest residence time on the column and elute together as the last peak in the chromatogram. This last peak in the chromatogram determines the total permeation limit.

One requirement for SEC is that the analyte does not interact with the surface of the stationary phases. Differences in elution time are based solely on the volume the analyte "sees". Thus, a small molecule that can penetrate every corner of the pore system of the stationary phase "sees" the entire pore volume and the interparticle volume, and will elute late (when the pore- and interparticle volume has passed through the column ~80% of the column volume). On the other extreme, a very large molecule that cannot penetrate the pore system "sees" only the interparticle volume (~35% of the column volume) and will elute earlier when this volume of mobile phase has passed through the column. The underlying principle of SEC is that particles of different sizes will elute (filter) through a stationary phase at different rates. This results in the separation of a solution of particles based on size. Provided that all the particles are loaded simultaneously or near-simultaneously, particles of the same size should elute together.

Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

Also, typically the stationary-phase particles are not ideally defined; both particles and pores may vary in size. The stationary phase may also interact in undesirable ways with a particle and influence retention times, though great care is usually taken to use stationary phases that are inert and minimize this issue.

Electrophoresis is a method which separates macromolecules by their charge and size. In gel electrophoresis an electric field is used to "pull" or "push" molecules through the gel, depending on their electrical charges. "Electrophoresis" refers to the electromotive force (EMF) that is used to move the molecules through the gel matrix. Using an electric field, molecules (such as DNA) can be made to move through a gel. The molecules being sorted are dispensed into a well in the gel material. The gel is placed in an electrophoresis chamber, which is then connected to a power source. By applying an electric field, the molecules will move through the matrix at different rates, determined largely by their mass when the charge to mass ratio (Z) of all species is uniform, toward the anode if negatively charged or toward the cathode if positively charged. The different sized molecules form distinct bands on the gel.

Gel electrophoresis refers to using a gel as an anticonvective medium and/or sieving medium, which can also be called stationary phase, during electrophoresis. The term "gel" in this instance refers to the matrix used to contain then separate the target molecules. In most cases, the gel is a cross-linked polymer whose composition and porosity is chosen based on the specific weight and composition of the target to be analyzed. When separating proteins or small nucleic acids the gel is usually composed of different concentrations of acrylamide and a cross-linker, producing different sized mesh networks of polyacrylamide. When separating larger nucleic acids, the preferred matrix is purified agarose. In both cases, the gel forms a solid, yet porous matrix. Acrylamide, in contrast to polyacrylamide, is a neurotoxin and must be handled using appropriate safety precautions to avoid poisoning.

After the electrophoresis is complete, the molecules in the gel can be stained to make them visible. For example, ethidium bromide, silver, or Coomassie brilliant blue dye may be used for this process. Other methods may also be used to visualize the separation of the mixture's components on the gel. If the analyte molecules fluoresce under ultraviolet light, a photograph can be taken of the gel under ultraviolet lighting conditions, often using a Gel Doc. If the molecules to be separated contain radioactivity added for visibility, an autoradiogram can be recorded of the gel.

If several samples have been loaded into adjacent wells in the gel, they will run parallel in individual lanes. Depending on the number of different molecules, each lane shows separation of the components from the original mixture as one or more distinct bands, one band per component. Incomplete separation of the components can lead to overlapping bands, or to indistinguishable smears representing multiple unresolved components.

Bands in different lanes that end up at the same distance from the top contain molecules that passed through the gel with the same speed, which usually means they are approximately the same size. There are molecular weight size markers available that contain a mixture of molecules of known sizes. If such a marker was run on one lane in the gel parallel to the unknown samples, the bands observed can be compared to those of the unknown in order to determine their size. The distance a band travels is approximately inversely proportional to the logarithm of the size of the molecule.

Gel electrophoresis is most commonly used for separation of biological macromolecules such as deoxyribonucleic acid (DNA), ribonucleic acid (RNA), or protein; however, gel electrophoresis can be used for separation of nanoparticles as well. Gels suppress the thermal convection caused by application of the electric field, and can also act as a sieving medium, retarding the passage of molecules; gels can also simply serve to maintain the finished separation, so that a post electrophoresis stain can be applied. DNA Gel electrophoresis is usually performed for analytical purposes, often after amplification of DNA via PCR, but may be used as a preparative technique prior to use of other methods such as mass spectrometry, RFLP, PCR, cloning, DNA sequencing, or Southern blotting for further characterization.

Gel electrophoresis is typically used in forensic, molecular biology, genetics, microbiology and biochemistry applications. The results can be analyzed quantitatively by visualizing the gel with UV light and a gel imaging device. The image is recorded with a computer operated camera, and the intensity of the band or spot of interest is measured and compared against standard or markers loaded on the same gel. The measurement and analysis are mostly done with specialized software.

Depending on the type of analysis being performed, other techniques are often implemented in conjunction with the results of gel electrophoresis, providing a wide range of field-specific applications.

SDS-PAGE, sodium dodecyl sulfate polyacrylamide gel electrophoresis, is a technique widely used particularly in forensic, molecular biology, genetics, and biochemistry to separate components according to their electrophoretic mobility (a function of length of polypeptide chain or molecular weight). SDS gel electrophoresis of samples that have identical charge per unit mass due to binding of SDS, results in fractionation by size.

Two-dimensional gel electrophoresis, abbreviated as 2-DE or 2-D electrophoresis, is a form of gel electrophoresis commonly used to analyze proteins. Mixtures of proteins are separated by two properties in two dimensions on 2D gels.

Temperature Gradient Gel Electrophoresis (TGGE) and Denaturing Gradient Gel Electrophoresis (DGGE) are forms of electrophoresis which use either a temperature or chemical gradient to denature the sample as it moves across an acrylamide gel. TGGE and DGGE can be applied to nucleic acids such as DNA and RNA, and (less commonly) proteins. TGGE relies on temperature dependent changes in structure to separate nucleic acids. DGGE was the original technique, and TGGE a refinement of it.

Agar is a linear and non-ionic polysaccharide consisting of D-galactose and 3,6-anhydro-L-galactose and it is produced from seaweeds. Agarose based electrophoresis gels are typically used in molecular biology laboratories, in methods comprising the separation of various sized DNA fragments, which are thereafter cut out from the gel, isolated and subsequently used for various purposes. The use of agarose requires warming of the agarose suspension before casting of the gel. However, warming destroys the intercalating dye which is added to the gel for DNA detection. Further, for isolating a desired DNA fragment from the gel it has to be cut mechanically out from the gel under strong UV light and in the presence of the dye. Further, in order to separate the DNA fragments from the gel for further use the gel must be removed.

Other gels used earlier for electrophoresis include starch gels.

Polyacrylamide gels are commonly used for electrophoresis particularly in the separation of nucleic acids. In general, stock solutions containing acrylamide monomer, a crosslinker such as bisacrylamide, gel buffers, and modifying agents such as sodium dodecyl sulphate ("SDS") are prepared. To manufacture a gel, the stock solutions are mixed with water in proportions according to the final desired concentrations of the various constituents and the polymerization reaction is effected.

The resolving power of the gel is determined by the content of agarose in the gel in the case of agarose gels. In contrast, the resolving power of polyacrylamide gels is adjusted by the mixing ratio of acrylamide to bisacrylamide.

US 2010/0236932 publication proposes composite gels comprising acrylamide or N-modified acrylamide, agarose, buffers and photo-initiators with or without cross-linkers.

The detection of nucleic acids in nucleic acid analytics with the aid of gel electrophoresis is based on the fact that fluorescent DNA binding dyes permanently bind non-covalently to nucleic acids and, in their bound form, enable nucleic acids to be located in the gel matrix after excitation with light of a suitable wavelength.

Ethidium bromide is typically used as the intercalating dye, however, it is neurotoxic and carcinogenic. Due to the toxicity, alternative DNA binding dyes such as for example SYBR Green or SYBR Gold (Molecular Probes, Inc.) are also used, the binding properties of which are not or not exclusively based on the principle of DNA intercalation.

The dyes used for electrophoresis are either admixed with the gel preparation before polymerization in the case of ethidium bromide, or the gel is stained after completion of the gel electrophoresis with the aid of an aqueous dye solution containing ethidium bromide or another dye. Furthermore, SYBR Green I can be added to the sample containing the nucleic acid before loading the gel.

Ion exchange chromatography is a popular method for the purification of proteins and other charged molecules. In cation exchange chromatography positively charged molecules are attracted to a negatively charged solid support (stationary phase). Conversely, in anion exchange chromatography, negatively charged molecules are attracted to a positively charged solid support.

To optimize binding of all charged molecules, the mobile phase is generally a low to medium conductivity solution. The adsorption of the molecules to the solid support is driven by the ionic interaction between the oppositely charged ionic groups in the sample molecule and in the functional group on the support. The strength of the interaction is determined by the number and location of the charges on the molecule and on the functional group. By increasing the salt concentration the molecules with the weakest ionic interactions start to elute from the column first. Molecules that have a stronger ionic interaction require a higher salt concentration and elute later in the gradient. The binding capacities of ion exchange resins are generally quite high. This is of major importance in process scale chromatography, but is not critical for analytical scale separations.

As a rule, the pH of the mobile phase buffer must be between the pI (isoelectric point) or pKa (acid dissociation constant) of the charged molecule and the pKa of the charged group on the solid support. For example, in cation exchange chromatography, using a functional group on the solid support with a pKa of 1.2, a sample molecule with a pI of 8.2 may be run in a mobile phase buffer of pH 6.0. In anion exchange chromatography a molecule with a pI of 6.8 may be run in a mobile phase buffer at pH 8.0 when the pKa of the solid support is 10.3.

For example, a protein sample is injected onto the column under conditions where it will be strongly retained. A gradient of linearly increasing salt concentration is then applied to elute the sample components from the column. An alternative to using a linear gradient is to use a step gradient. This requires less complicated equipment and can be very effective to elute different fractions if the appropriate concentrations of salt are known, usually from linear gradient experiments.

Also changes in pH are used to affect separation. In cation exchange chromatography, raising the pH of the mobile phase buffer will cause the molecule to become less protonated and hence less positively charged. The result is that the protein no longer can form ionic interaction with the negatively charged solid support, which ultimately results in the molecule to elute from the column. In anion exchange chromatography, lowering the pH of the mobile phase buffer will cause the molecule to become more protonated and hence more positively charged. The result is that the protein no longer can form ionic interaction with the positively charged solid support which causes the molecule to elute from the column.

Affinity chromatography is a method of separating biochemical mixtures and it is based on a highly specific interaction such as that between antigen and antibody, enzyme and substrate, or receptor and ligand. The immobile (stationary) phase is typically a gel matrix, often of agarose. Usually the starting point is an undefined heterogeneous group of molecules in solution, such as a cell lysate, growth medium or blood serum. The molecule of interest will have a well known and defined property which can be exploited during the affinity purification process. The process itself can be thought of as an entrapment, with the target molecule becoming trapped on a solid or stationary phase or medium. The other molecules in solution will not become trapped as they do not possess this property. The solid medium can then be removed from the mixture, washed and the target molecule released from the entrapment in a process known as elution. Possibly the most common use of affinity chromatography is for the purification of recombinant proteins. Binding to the solid phase may be achieved by column chromatography whereby the solid medium is packed onto a column, the initial mixture run through the column to allow setting, a wash buffer run through the column and the elution buffer subsequently applied to the column and collected. Alternatively binding may be achieved using a batch treatment, by adding the initial mixture to the solid phase in a vessel, mixing, separating the solid phase (for example), removing the liquid phase, washing, re-centrifuging, adding the elution buffer, re-centrifuging and removing the eluate.

Sometimes a hybrid method is employed, the binding is done by the batch method, then the solid phase with the target molecule bound is packed onto a column and washing and elution are done on the column.

A third method, expanded bed adsorption, which combines the advantages of the two methods mentioned above, has also been developed. The solid phase particles are placed in a column where liquid phase is pumped in from the bottom and exits at the top. The gravity of the particles ensure that the solid phase does not exit the column with the liquid phase.

Affinity columns can be eluted by changing the ionic strength through a gradient. Salt concentrations, pH, pI, charge and ionic strength can all be used to separate or form the gradient to separate.

Affinity chromatography can be used in a number of applications, including nucleic acid purification, protein purification from cell free extracts, and purification from blood.

Another use for the procedure is the affinity purification of antibodies from blood serum. If serum is known to contain antibodies against a specific antigen (for example if the serum comes from an organism immunized against the antigen concerned) then it can be used for the affinity purification of that antigen. This is also known as immunoaffinity chromatography.

Immobilized metal ion affinity chromatography (IMAC) is based on the specific coordinate covalent bond of amino acids, particularly histidine, to metals. This technique works by allowing proteins with an affinity for metal ions to be retained in a column containing immobilized metal ions, such as cobalt, nickel, copper for the purification of histidine containing proteins or peptides, iron,zinc or gallium for the purification of phosphorylated proteins or peptides. Many naturally occurring proteins do not have an affinity for metal ions, therefore recombinant DNA technology cab be used to introduce such a protein tag into the relevant gene. Methods used to elute the protein of interest include changing the pH, or adding a competitive molecule, such as imidazole.

Based on the above it can be seen that stationary phases are necessary in several separation methods. In the methods a stationary phase provides means for separating components in an efficient way from a mixture which is conducted through the stationary phase, yet not interacting with the components in an undesired way. There is an evident need for improved stationary phases useful in separation methods, particularly in methods based on electrophoresis or chromatography.

SUMMARY

Aspects of the invention are directed to the use of a stationary phase comprising fibril cellulose in separation methods. The invention relates to the use and method of using a stationary phase comprising fibril cellulose in separation methods based on electrophoresis or chromatography. Said stationary phase comprising fibril cellulose may be used in said methods for separating and/or analyzing and/or fractionating of synthetic and natural polymers, macromolecules, biomolecules and nanoparticles.

A stationary phase comprising fibril cellulose may be used as gel electrophoresis matrix or media. In addition to conventional gel electrophoresis methods, both one dimensional and two dimensional, also temperature gradient gel electrophoresis and denaturing gradient gel electrophoresis as well as DNA gel electrophoresis may be carried out with a stationary phase comprising fibril cellulose. The DNA gel electrophoresis is usually performed for analytical purposes, often after amplification of DNA via PCR, but may be used as a preparative technique prior to use of other methods such as mass spectrometry, RFLP, PCR, cloning, DNA sequencing, or Southern blotting for further characterization.

A stationary phase comprising fibril cellulose may be used as a stationary phase in methods based on chromatography, where the chromatographic method may be based on exclusion chromatography, ion exchange chromatography or affinity chromatography.

In the chromatographic methods the fractions or components which are separated are brought into contact with the stationary phase and a mobile phase is allowed to pass through the stationary phase. The stationary phase may be packed in a vessel where the separation is carried out, suitably in a column. Suitably a mobile phase comprising, in liquid form, a mixture, which is separated and/or analyzed and optionally at least one solvent is passed through the stationary phase, optionally using pressure. Fractions, separated according to their molecular size and/or charge and/or affinity and/or hydrophobicity may be obtained.

Further aspects of the invention are directed to a method for analyzing and/or separating and/or fractionating components selected from natural polymers, synthetic polymers, macromolecules, biomolecules and nanoparticles, said method comprising the steps of carrying out electrophoresis where a stationary phase comprising fibril cellulose is used as gel electrophoresis matrix, a mixture comprising the components is brought into contact with the stationary phase, an electrical field is applied on the matrix whereby the components are separated. The separated components may be removed from the matrix.

Still further aspects of the invention are directed to a method for analyzing and/or separating and/or fractionating components selected from natural polymers, synthetic polymers, macromolecules, biomolecules and nanoparticles, said method comprising the steps of carrying out a chromatographic method based on exclusion chromatography, ion exchange chromatography or affinity chromatography, wherein a mobile phase comprising in liquid form a mixture comprising the components, and optionally at least one solvent, is passed through the stationary phase comprising fibril cellulose, optionally using pressure whereby the components are separated. The separated components may be fractionated.

The invention is further directed to a vessel comprising a stationary phase comprising fibril cellulose, suitably a prepacked column filled with fibril cellulose. Said vessel or column comprises additionally at least one filter arranged at one end of the vessel or column for keeping the stationary phase therein.

Further, the invention is directed to a kit for gel electrophoresis, comprising a stationary phase comprising fibril cellulose and reagents.

The characteristic features of the invention are presented in the appended claims.

BRIEF DESCRIPTION OF THE DRAWINGS

FIG. 4 illustrates graphically quantitative PCR run from *C. perfringens* dilution series that show strong linear correlation between the dilution and the PCR response in the presence or absence of 1.5 wt % fibril cellulose.

FIG. 5 depicts diffusion of different molecular weight dextrans (20 kDa, 70 kDa, and 250 kDa) through 1 wt % native fibril cellulose hydrogel.

DEFINITIONS

Unless otherwise specified, the terms, which are used in the specification and claims, have the meanings commonly used in the field. Specifically, the following terms have the meanings indicated below.

The term "stationary phase" refers here to an "immobile phase" or anticonvective medium and/or sieving medium.

The term "mobile phase" refers here to liquid medium, which may comprise one or more component in liquid form. Typically the mobile phase is allowed to move through the stationary phase As used herein, the term "fibril cellulose" is understood to encompass all microfibrillated celluloses (MFC) and nanocelluloses. Further, there are several other widely used synonyms for fibril cellulose. For example: cellulose nanofiber, nanofibrillated cellulose (CNF), nanofibrillar cellulose (NFC), nano-scale fibrillated cellulose, microfibrillar cellulose, or cellulose microfibrils.

Fibril cellulose produced by certain microbes has also various synonyms, for example, bacterial cellulose (BC), microbial cellulose (MC), biocellulose, nata de coco (NDC), or coco de nata (CDN).

DETAILED DESCRIPTION OF THE INVENTION

It was surprisingly found that fibril cellulose can be used for providing a stationary phase particularly suitable for several separation methods. Fibril cellulose forms readily a stable gel in polar solvents and water. The properties of the gel may be varied according to the desired separation method and compounds to be separated or analyzed. Particularly the invention is directed to the use of a stationary phase comprising fibril cellulose in separation methods. Said separation methods are suitably based on electrophoresis or chromatography. Said chromatographic methods may suitably be selected from methods based on exclusion chromatography, ion exchange chromatography or affinity chromatography. Said methods are particularly useful in analyzing, separation and fractionation of natural polymers, synthetic polymers, macromolecules, biomolecules and nanoparticles and charged particles or compounds, including also preparative chromatographic methods. Electrophoresis includes here gel electrophoresis, temperature gradient gel electrophoresis, denaturing gradient gel electrophoresis and two-dimensional gel electrophoresis and DNA gel electrophoresis.

Exclusion chromatography includes size-exclusion chromatography, which may also be called as gel-filtration chromatography or gel-permeation chromatography.

Ion exchange chromatography includes here anion exchange chromatography and cation exchange chromatography.

Affinity chromatography includes here affinity chromatography, immunoaffinity chromatography and immobilized metal ion affinity chromatography.

Fibril cellulose is obtained from any non-animal based cellulose raw material.

The term "cellulose raw material" refers to any cellulose raw material source that can be used in production of cellulose pulp, refined pulp, and fibril cellulose. The cellulose raw material may be based on any plant material that contains cellulose or any microbial cellulose.

Plant material may be wood and said wood can be from softwood tree such as spruce, pine, fir, larch, douglas-fir or hemlock, or from hardwood tree such as birch, aspen, poplar, alder, eucalyptus or acacia, or from a mixture of softwoods and hardwoods.

Non-wood material can be from agricultural residues, grasses or other plant substances such as straw, leaves, bark, seeds, hulls, flowers, vegetables or fruits from cotton, corn, wheat, oat, rye, barley, rice, flax, hemp, manilla hemp, sisal hemp, jute, ramie, kenaf, bagasse, bamboo or reed.

The cellulose raw material may be also derived from the cellulose-producing micro-organism, such as from bacterial fermentation processes. The micro-organisms can be of the genus *Acetobacter, Agrobacterium, Rhizobium, Pseudomonas* or *Alcaligenes*, preferably of the genus *Acetobacter* and more preferably of the species *Acetobacter xylinum* or *Acetobacter pasteurianus*.

The term "cellulose pulp" refers to cellulose fibers, which are isolated from any cellulose raw material using chemical, mechanical, thermo-mechanical, or chemi-thermo-mechanical pulping processes. Cellulose pulp, which can be pulp of plant origin, especially wood (softwood or hardwood pulp, for example bleached birch pulp) and where the cellulose molecules are oxidized in one of the above-described methods, is easy to disintegrate to fibril cellulose.

The term "fibril cellulose" refers to a collection of isolated cellulose microfibrils (nanofibers) or microfibril bundles derived from cellulose raw material. Microfibrils have typically high aspect ratio: the length exceeds one micrometer while the number-average diameter is typically below 200 nm. The diameter of microfibril bundles can also be larger but generally less than 1 μm. The smallest microfibrils are similar to so called elementary fibrils, which are typically 2-12 nm in diameter. The dimensions of the fibrils or fibril bundles are dependent on raw material and disintegration method.

Fibril cellulose is characterized by very high water retention values, a high degree of chemical accessibility and the ability to form stable gels in water or other polar solvents. Fibril cellulose product is typically a dense network of highly fibrillated celluloses. The fibril cellulose may also contain some hemicelluloses; the amount is dependent on the plant source.

To obtain fibril cellulose mechanical disintegration of cellulose pulp, oxidized cellulose raw material or microbial cellulose is carried out with suitable equipment such as a refiner, grinder, homogenizer, colloider, friction grinder, ultrasound-sonicator, fluidizer such as microfluidizer, macrofluidizer or fluidizer-type homogenizer. Preferably mechanically disintegrated fibril cellulose is used.

Several different grades of fibril celluloses have been developed using various production techniques. The grades have different properties depending on the manufacturing method, degree of fibrillation and chemical composition. The chemical compositions of the grades also vary. Depending on the raw material source, e.g. HW vs. SW pulp, different polysaccharide composition exists in the final fibril cellulose product. Typically, non-ionic or native or neutral grades have wider fibril diameter while the chemically modified grades are a lot thinner. Size distribution is also narrower for the modified grades.

The "fibril cellulose" refers here to one grade of fibril cellulose or a combination of two or more different grades of fibril cellulose. For example modified grades of fibril cellulose may be blended with native grade for enhancing binding of certain compounds to the gel or binding of some specific impurities etc.

According to one embodiment of the invention plant derived native fibril cellulose may be used, suitably as a gel, such as a hydrogel (aqueous gel).

Fibril cellulose is understood to encompass here also any chemically or physically modified derivates of cellulose, cellulose nanofibers or nanofiber bundles, obtained from any cellulose raw materials. The chemical modification may be based for example on carboxymethylation, oxidation, (TEMPO-oxidation), esterification, or etherification reaction of cellulose molecules, whereby aninically or cationically modified grades are obtained. Modification may also be realized by physical adsorption of anionic, cationic, or non-ionic substances or any combination of these on cellulose surface. The described modification can be carried out before, after, or during the production of cellulose nanofibers. Certain modifications may lead to materials that are degradable in human body. Modified grades are typically prepared from bleached pulps. In the modified grades, the hemicelluloses are also modified together with the cellulose domain. Most probably, the modification is not homogeneous, i.e. some parts are more modified than others. Thus, detailed chemical analysis is not possible-the modified products are always complicated mixtures of different polysaccharide structures.

Chemically modified grades, such as anionic and cationic grades typically have their surface charge modified and they may suitably be used as dry powder or an aqueous gel. Chemically modified grades may be used particularly in the separation of compounds, where a specific surface charge enhances the separation. Thus suitable fibril cellulose or a combination of different fibril celluloses may de selected and designed for this purpose according to the type of the compounds to be separated. Dry powders of fibril cellulose may conveniently be manufactured by spray drying and/or lyophilization of suspension or dispersions containing said fibril cellulose, using any conventional methods known in the art. Suitably the chemically modified grades are spray dried and optionally granulated to small beads. These may be reconstituted into gel with a polar solvent, suitably water.

The fibril cellulose gel or hydrogel refers here to a dispersion of fibril cellulose. The fibril cellulose has excellent gelling ability, which means that it forms a hydrogel already at a low consistency in an aqueous medium.

Suitably the cellulose raw material such as cellulose pulp is pretreated with acid and base prior to the mechanical disintegration. The pretreatment is effected by subjecting the cellulose pulp to acid treatment, preferably with hydrochloric acid for removing any positively charged ions having a charge more than +1, followed by treatment with an inorganic base containing positively charged ions having a charge +1, preferably NaOH, where $Na^+$ ions replace the earlier ions. The absence of any positively charged ions having a charge more than +1 is particularly advantageous in life science and molecular biology applications where complex formation of DNA with ions with charges more than +1 can be avoided. The pretreatment provides the final product excellent gelling properties and transparency. The fibril cellulose obtained from pretreated cellulose raw material is referred to here as ion exchanged fibril cellulose. According to one embodiment of the invention ion exchanged fibril cellulose is used.

Microbial purity of fibril cellulose is often essential. Therefore, fibril cellulose may be sterilized prior to use, suitably in a gel form. In addition, it is important to minimize the microbial contamination of the product before and during the mechanical disintegration, such as fibrillation. Prior to fibrillation/mechanical disintegration, it is advantageous to aseptically collect the cellulose pulp from the pulp mill immediately after bleaching stage when the pulp is still sterile.

Fibril cellulose hydrogels have typically remarkable high yield stress and high zero-shear viscosity at low concentrations. Thus, i.e. if gas bubbles are generated in the fibril cellulose hydrogels they may stay still for long periods of time. The buoyancy of gas bubbles can be, however, easily increased by lowering gas pressure (e.g. 15 mmHg) above the gel, which lowers the solubility of gas in the hydrogels phase and, respectively increases the volumes of initial gas bubbles. The increased gas bubbles escape easily to upper gas phase.

The stationary phase comprising fibril cellulose may comprise one grade of fibril cellulose or a combination of different grades, such as native and modified grades (anionic grade, cationic grade etc.).

Modified grades and native or non-ionic grades may be used in gel electrophoresis methods, however native grades are particularly suitable.

In exclusion chromatographic and affinity chromatographic methods the selection of the fibril cellulose grade depends on the compounds, which are analyzed or separated. In size exclusion chromatography suitably native or non-ionic grade of fibril cellulose is used.

In ion-exchange chromatography the modified grades, such as anionic or cationic grades may be suitable. The modified grades may be regenerated after the separation or analysis in a similar manner as conventional ion-exchange resins, followed by reuse.

The stationary phase may comprise the fibril cellulose as a gel, preferably a hydrogel, or alternatively as a dry powder, which may be reconstituted prior use to a gel by bringing it in contact with a polar solvent or a mixture thereof, suitably water whereby a hydrogel is obtained. Particularly suitably the modified grades, such as anionic and cationic grades, are provided as dry powder. The native and non-ionic grades are suitably provided as gels, such as hydrogels.

The number average fibril diameter of the fibril cellulose in a stationary phase is selected according to the requirements of the separation method, thus a suitable stationary phase may be designed for each specific method, taking into account for example the chromatographic requirements, desired resolution, properties of the compounds which are separated etc. The number average fibril diameter of the fibril cellulose may range from 1 to 1000 nm, suitably from 1 to 200 nm, and according to one embodiment the number average fibril diameter of native grades is from 1 to 100 nm, and in chemically modified grades from 1 to 20 nm.

The stationary phase may comprise 0.05-100 wt % of at least one grade of fibril cellulose. The stationary phase may optionally comprise additives.

Suitably, in gel electrophoresis, a gel comprising 0.05-20 wt %, suitably 0.1-3 wt % and according to one embodiment 0.5-1.5 wt % of fibril cellulose is used as stationary phase. Suitably the fibril cellulose is native or non-ionic fibril cellulose. The stationary phase may optionally comprise additives, such as dyes, markers, activated carbon etc. The gel may be a ready-to-use casted gel, which may additionally be sterilized and packed in sterile packages, or it may be packed as a hydrogel in a syringe, which can be used for the application of the gel. The gel may also be used in combination with conventional gels, such as agarose or polyacrylamide gels, for example as sections in said gels. The gel may also be in the form of a dry membrane which can be reconstituted with water prior to use. Anionic grades, such as carboxymethylated fibril cellulose may be used for dry membranes.

After running the gel electrophoresis, separated compounds can easily be removed for example by pipetting, followed by suitable rework, purification etc. The stationary phase comprising fibril cellulose may be used in any gel electrophoresis applications known in the art. Particularly suitably the stationary phase comprising fibril cellulose may be used in application in the field of forensic, molecular biology, genetics, microbiology and biochemistry.

Further, the stationary phase comprising fibril cellulose may be incorporated in a gel electrophoresis kit, which comprises reagents necessary for carrying out the gel electrophoresis and the stationary phase comprising fibril cellulose as precasted gel or provided as hydrogel, suitably in a dispenser such as in a syringe.

In exclusion chromatography dry powder or beads or a gel comprising 0.05-50 wt %, suitably 1-30 wt % and according to one embodiment 2-20 wt % of fibril cellulose may be used as the stationary phase. The stationary phase in the form of dry powder or beads may be reconstituted prior use to a gel by bringing it in contact with a polar solvent or a mixture thereof, suitably water. The stationary phase may optionally comprise additives, such as dyes, markers, activated carbon etc. The dry powder or beads, or the hydrogel comprising the fibril cellulose may easily be packed in a vessel, such as a column, having at least one filter arranged therein, preferably at the other end (bottom) of the column for keeping the fibril cellulose therein. Accordingly ready-to-use prepacked columns, which may also be sterilized, may be provided to end users. The stationary phase comprising fibril cellulose may be used in any exclusion chromatography applications known in the art.

In ion exchange chromatography dry powder or beads or a gel comprising 0.05-50 wt %, suitably 1-30 wt % and according to one embodiment 2-20 wt % of fibril cellulose may be used as stationary phase. The dry powder or beads may be reconstituted prior use to a gel by bringing it in contact with a polar solvent or a mixture thereof, preferably water. The stationary phase may optionally comprise additives, such as dyes, markers, activated carbon etc. The dry powder or beads, or the hydrogel comprising the fibril cellulose may easily be packed in a vessel, such as a column, having at least one filter arranged therein, preferably at the other end (bottom) of the column for keeping the fibril cellulose therein. Accordingly ready-to-use prepacked columns, which may also be sterilized, may be provided to end users. The stationary phase comprising fibril cellulose may be used in any ion exchange chromatography applications known in the art, including large scale applications for the separation of charged particles, charged ion or charged compounds from mixtures.

In applications based on affinity chromatography dry powder or beads or elements or a gel comprising 0.05-50 wt %, suitably 1-30 wt % and according to one embodiment 2-20 wt % of fibril cellulose may be used as the stationary phase. The stationary phase in the form of dry powder or beads or elements may be reconstituted prior use to a gel by bringing it in contact with a polar solvent or a mixture thereof, suitably water. The stationary phase may optionally comprise additives, such as dyes, markers, activated carbon etc. The dry powder or beads or the hydrogel comprising the fibril cellulose may easily be packed in a vessel, such as a column, having at least one filter arranged therein, preferably at the other end (bottom) of the column for keeping the fibril cellulose therein. Accordingly ready-to-use prepacked columns, which may also be sterilized, may be provided to end users. The stationary phase comprising fibril cellulose may be used in any affinity chromatography applications known in the art.

The elements may be obtained by casting the gel and drying it or by extrusion of a fibril cellulose gel into an organic solvent.

The hydrogel comprising fibril cellulose can very easily be dispersed, or injected in a column for example with a syringe.

The stationary phase comprising fibril cellulose may suitably also be used in separation methods on a larger industrial scale, in process scale applications, particularly in the field of dairy industry for separation of proteins, in the separation and fractionation of carbohydrates and other synthetic and natural polymers, biomolecules, macromolecules and nanoparticles, and in purification methods of liquids and mixtures, where separation of charged particles, charged ions such as metal ions or charged compounds is desired.

The used stationary phase, containing for example protein or carbohydrate fractions or residues may easily be taken out from the process equipment for example by draining and it may conducted for further use, such as a component in animal feeds, particularly in the case non-pathogenic and non-toxic ingredients were used in the separation method.

The working range pH of the stationary phase may be adjusted by selecting a suitably modified grade of fibril cellulose.

The diffusion rate may be adjusted by selecting a suitable chemically modified fibril cellulose grade or a combination of fibril celluloses, suitable number average fibril size range of the fibril cellulose, suitable force which is used for driving the mobile phase through the stationary phase, for example pressure, gravity, electromotive force, etc.

The use of stationary phase comprising fibril cellulose in separation methods based on gel electrophoresis or exclusion chromatography or ion exchange chromatography provides several valuable effects. As fibril cellulose is not a polymerization product, there are no monomer residues, such as neurotoxic acrylamide, left in the product. With regard to nucleic acid analysis and isolation, the risk of potential enumeration and detection problems can be avoided or at least significantly reduced by the use of a stationary phase comprising fibril cellulose in the separation methods.

The stationary phase comprising fibril cellulose is a nontoxic product, which is easy to manufacture, easy to handle and requires no specific precautions from the end user. Suitably the hydrogel may be injected to column, injected or casted or spread on plates and wells and it may be dispersed or pipetted. As can be seen from the examples it has no adverse effects and does not interfere with DNA isolation or PCR analysis, and in fact the use of fibril cellulose improves DNA isolation yields.

The material remaining in the stationary phase after separation may easily be removed or isolated by diluting with water, followed by decanting or centrifuging, or alternatively the fibril cellulose may be enzymatically degraded with for example cellulose enzymes.

In the case of gel electrophoresis, the bands containing the desired components obtained after the separation procedure can easily and exactly be drawn with a syringe and the components can be isolated from the hydrogel.

The following examples are illustrative of embodiments of the present invention, as described above, and they are not meant to limit the invention in any way.

EXAMPLES

Fibril cellulose samples: Native fibril cellulose was produced by high pressure homogenization (five subsequent cycles) of highly purified bleached birch pulp, followed by autoclave sterilization. After fluidization, the fibril cellulose was dilute hydrogel (1.8 wt %). Ion-exchanged native fibril cellulose was obtained in a similar manner but additionally prior to fibrillation it was subjected to acid-base treatment in order to remove high valency cations (method described in previous sections). After high pressure homogenization (15 subsequent cycles) the ion-exchanged fibril cellulose forms a strong hydrogel having lower turbidity compared to the other sample. Fibril cellulose was sterilized by autoclaving when necessary. Transparent anionic fibril cellulose was obtained as hydrogel (0.9 wt %) by similar homogenization process of a chemically modified cellulose pulp (TEMPO-oxidized cellulose pulp).

Example 1

Use of Electrophoresis Gel Matrix Based on Fibril Cellulose

Agarose gel containing 1.5% by weight of agarose was prepared according normal laboratory practice, after which two about 3 cm×5 cm slices of the gel were cut and removed from the central part of the gel. These two holes were filled with fibril cellulose hydrogel containing 1.5% by weight of native fibril cellulose and the whole gel system was immersed in 1×TAE buffer for electrophoresis. The selection of the fibril cellulose type and grade and mixing of the fibril cellulose hydrogel have impact on the turbidity, appearance and separation capability of the hydrogel. Preferably the mixing is carried out carefully in order to avoid any air bubbles in the gel, which may cause increased turbidity of the gel.

The gel was loaded with complete 16S gene *E. coli* gene (estimated MW about 1.4 kb) and taxonomically important smaller *C. perfringens* S16 fragment (estimated molecular weight about 0.6 kb). The electrophoresis was carried out and the gel was stained with ethidium bromide that makes DNA visible under UV-light. (A) the whole 16S gene, (B) 16S fragment and (C) dimer of 16S fragment (i.e. dimer of 16S fragment). The ladders are molecular weight markers.

The smaller 16S fragment contains two bands, the smaller is the actual fragment and the higher molecular weight fragment is its dimer. The gel was run at 120 volt until the ethidium bromide stained DNA fragments were clearly migrated inside the fibril cellulose matrix, after which the gel run was stopped and photographed, see FIG. 1.

Figure 1:
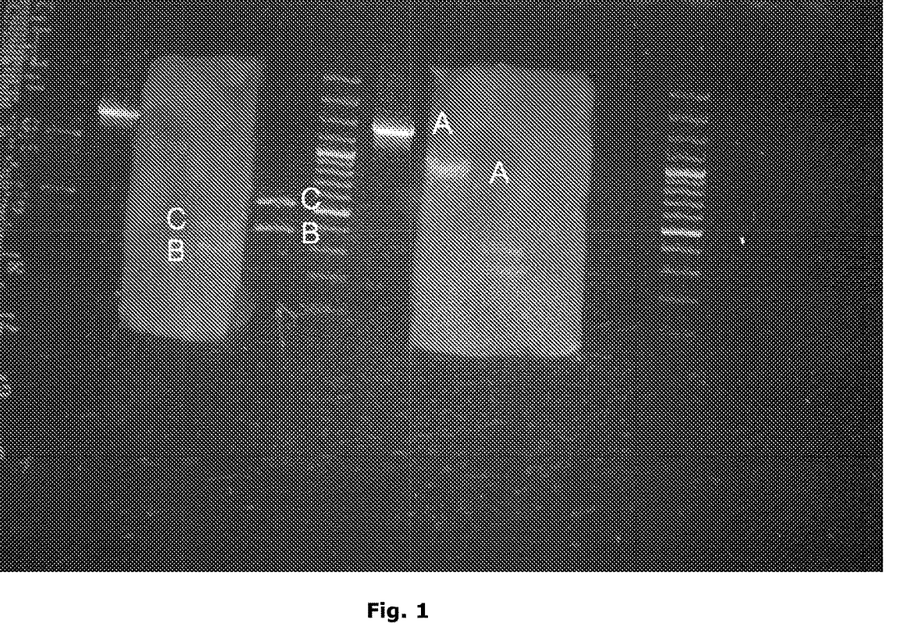
FIG. 1 depicts gel electrophoresis carried out with fibril cellulose gel matrix and agarose gel matrix. The gel was stained with ethidium bromide to make DNA visible under UV-light.

The stained gel demonstrates that the fibril cellulose matrix acts in a similar way as agarose and it is able to separate the DNA fragments based on their molecular weight. The DNA bands are little fainter in fibril cellulose, which is likely caused by lower transparency of the used fibril cellulose material. Furthermore, the migration rate is higher in fibril cellulose gel, which means that similar migration rate can be achieved by using more concentrated gel mixture.

Figure 2:
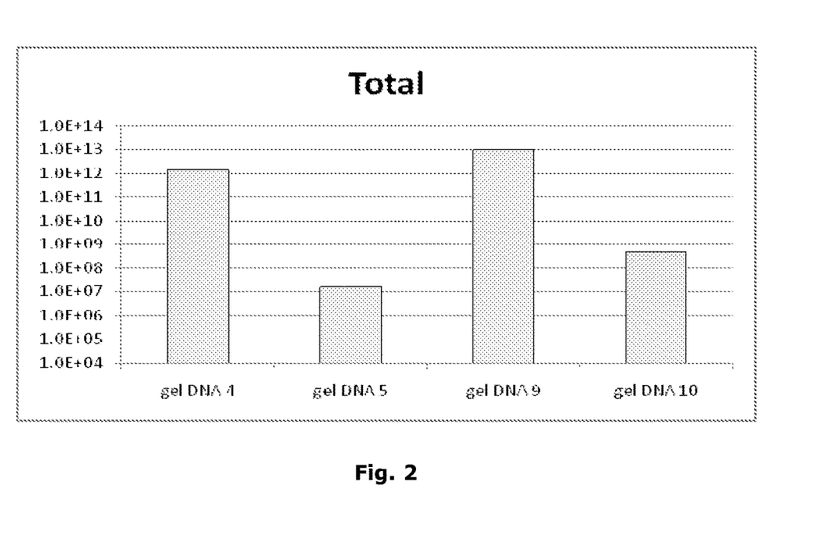
FIG. 2 illustrates graphically quantitative PCR analysis results of extracted DNA samples from fibril cellulose gel after gel electrophoresis.
Figure 3:
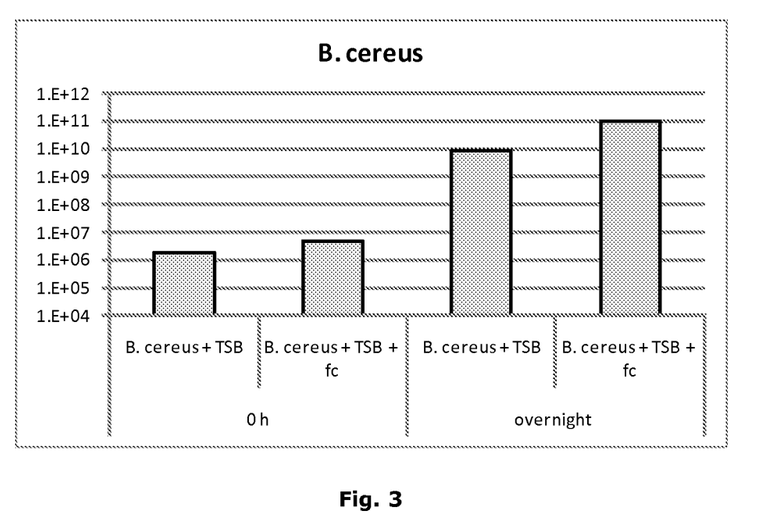
FIG. 3 illustrates graphically results of *B. cereus* enumeration, said *B. cereus* cultured in two media, one containing 1.5 wt % of fibril cellulose (fc) and one without.
Figure 4:
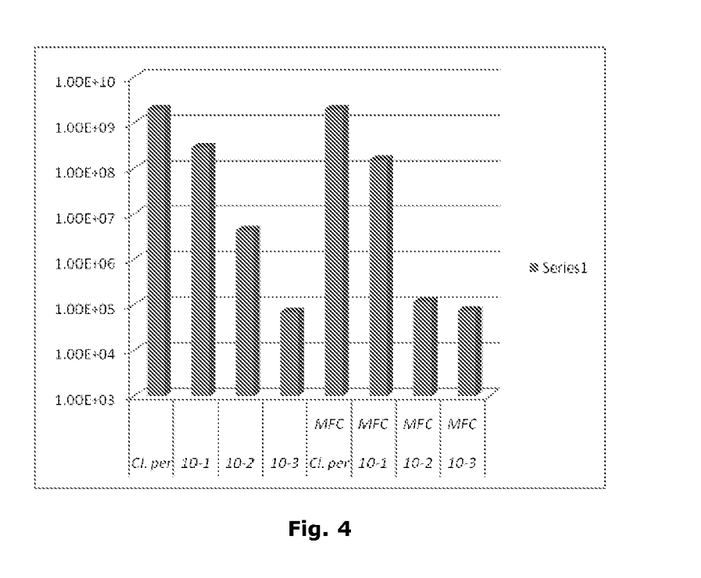

Next procedure was to isolate the DNA fragments from the gel. In agarose it requires mechanical cutting of gel material. In fibril cellulose the DNA fragments were simply pipetted out from the gel. This is clearly faster and easier. Thereafter quantitative PCR analysis of extracted DNA samples from fibril cellulose gel was carried out using universal primers and Sybergreen I chemistry as described above, see FIG. 2. The data indicates that almost same signal was gained from line 4 and 9 and from line 5 and 10, which show good reproducibility for extracted DNA fragments.

Example 2

Enumeration of Microorganisms from Fibril Cellulose Carrier

*Bacillus cereus* bacterium was cultivated in two different media, one containing 1.5 wt % of native fibril cellulose and one without it, and it was measured if the fibril cellulose was able to provide higher microbial cell numbers. PCR based enumeration was used in the trial and it provided excellent example of fibril cellulose's interaction with the PCR detection.

The growth medium used in the experiment was standard trypsin soy broth, and it was prepared according the manufacturer's instructions and autoclaved for sterility. Before autoclaving the growth medium was divided into the two parts, one of which 1.5 wt % of fibril cellulose was added. Small inoculum of *B. cereus* was grown overnight at 37° C. to reach dense microbial culture, and that was used to inoculate both growth media, about thousand fold dilution was used in the inoculation. Both test media were sampled 0 and 24 hours after the inoculation. 0.1 ml sample of culture was used for PCR based microbial enumeration. The enumeration method was based on the Ruminolyze protocol, where the microbial sample is first diluted to washing buffer, and microbial cells are pelleted by centrifugation (10 min 18 000×g). The supernatant is discarded and pellet is suspended to enzymatic lysis buffer and thereafter strongly beaten with glass beads in order to both enzymatically and mechanically lyse microbial cells to release their DNA content. The released DNA is purified with phenol-chloroform extraction, then precipitated with ethanol and finally dissolved to the DNA storage buffer. The *B. cereus* enumeration was performed with two *B. cereus* selective DNA primers and Sybergreen I chemistry. The results are shown in FIG. 3.

Accordingly *Bacillus cereus* cell numbers on growth media (TSB) and fibril cellulose (fc) in the beginning (0 h) and after overnight incubation were analyzed by quantitative PCR. The experiment indicates that small number of *B. cereus* cells, about $10^5$ cells/ml, can be detected in the presence of fibril cellulose that indicates that fibril cellulose has no effect on the sensitivity of the PCR assay. Furthermore, 24 hour sample gives higher cell numbers than the 0 hour sample. This means that the dynamic range of PCR is not disturbed by the presence of fibril cellulose and the fibril cellulose does not hinder the PCR reaction when is it run at its maximum speed, in other words when there are large amounts of template DNA. FIG. 3 also shows that more cells are counted in the presence of fibril cellulose at both 0 hours and 24 hours sampling points. This suggests that fibril cellulose aids the DNA isolation and provides higher DNA yields for *B. cereus* enumerations. This also suggests that fibril cellulose even improves PCR protocols.

Similar experiments were also performed with other bacterial species, *Clostridium perfringens, Lactobacillus salivarius* and *Desulfovibrio desulficans*. The results were similar to *B. cereus* findings, and they support the contention that the fibril cellulose does not inhibit DNA isolation or PCR procedures.

Example 3

Microbial Quantification in the Presence of Fibril Cellulose

Dilution series (10-, 100 and 1000-fold dilution) of dense *Clostridium perfringens* culture (about $10^9$ cells/ml) was prepared in the presence of 1.5 wt % of native fibril cellulose and without it. The diluted microbial samples were suspended to lysis buffer and glass beads and exposed to microbial DNA isolation method (as described in example 2 above). After the DNA isolation the DNA samples were used for PCR based enumeration by using *C. perfringens* specific primers and Sybergreen I chemistry. The results of PCR quantification are shown graphically in FIG. 4. The data shows strong linear correlation between PCR results and calculated dilution without any interference from fibril cellulose, i.e. between the dilution and the PCR response in the presence or absence of 1.5 wt % of fibril cellulose.

Example 4

Diffusion of Dextrans through Fibril Cellulose Hydrogels

Diffusion properties of fibril cellulose hydrogel were demonstrated with different molecular weight dextrans in the following manner:

400 μl of transparent or opaque fibril cellulose hydrogel (1 wt % native fibril cellulose) was planted per filter on the apical compartment in Transwell™ filter well plates (filter pore size 0.4 μm). 1 ml of PBS was added into the basolateral side and 100 μl (25 μg) of fluorescent labeled dextrans were added on top of the hydrogels (MW of 20 k, 70 k and 250 k). Plate was fixed firmly and left undisturbed on a well plate rocker. 100 µl samples were taken from the basolateral side and equal amount was replaced with PBS. First samples were taken with 15 minute intervals, other samples were taken with different time points ranging from 30 minutes to 2 hours and final samples at 24 hours. Total of 168 samples were taken. Target plate (OptiPlate™-96 F) was measured at excitation and emission wavelengths 490 nm and 520 nm respectively.

Figure 5:
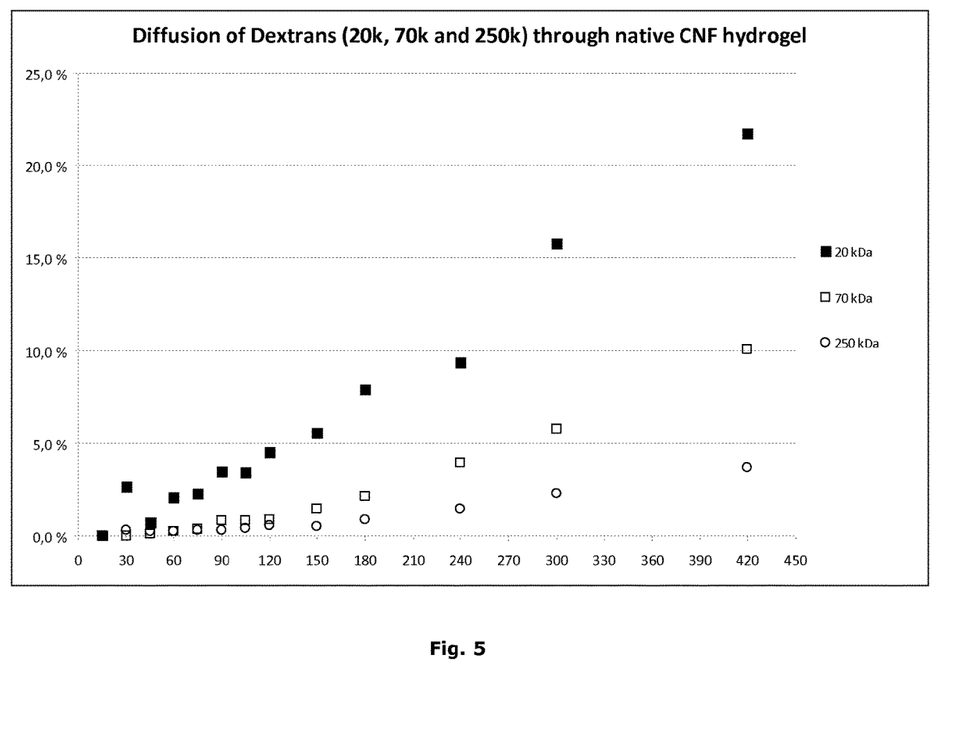

Diffusion of different molecular weight dextrans through 1% native fibril cellulose gel is presented in FIG. 5. The diffusion of the model compounds takes place at constant rate and it is highly dependent on the molecular weight (size) of the compound. It is clear that in the CNF hydrogels molecules are able to diffuse efficiently although the gel structure is firm enough to stabilize the cell suspension.

The diffusion of compounds can be controlled as a function of the size of the molecule (protein) or as a hydrogel concentration.

While the invention has been described with respect to specific examples including presently preferred modes of carrying out the invention, those skilled in the art will appreciate that there are numerous variations and permutations of the above described embodiments that fall within the spirit and scope of the invention. It should be understood that the invention is not limited in its application to the details of construction and arrangements of the components set forth herein. Variations and modifications of the foregoing are within the scope of the present invention.

The invention claimed is:

1. A separation method comprising:
separating two components by using a stationary phase comprising mechanically disintegrated nanofibrillar cellulose derived from plant material, wherein the stationary phase comprising mechanically disintegrated nanofibrillar cellulose is in the form of a hydrogel, the separation method being selected from methods based on electrophoresis or chromatography and the components being selected from synthetic polymers, natural polymers, macromolecules, biomolecules, nanoparticles, charged particles, charged ions, charged compound and combinations thereof.

2. The separation method according to claim 1, wherein the method based on electrophoresis is selected from gel electrophoresis, temperature gradient gel electrophoresis, denaturing gradient gel electrophoresis, two-dimensional gel electrophoresis and DNA gel electrophoresis.

3. The separation method according to claim 1, wherein the method based on chromatography is selected from exclusion chromatography, ion exchange chromatography and affinity chromatography.

4. The separation method according to claim 1 wherein the amount of the nanofibrillar cellulose in the stationary phase is from 0.05 to 50 wt %.

5. A method for separating components selected from synthetic polymers, natural polymers, macromolecules, biomolecules, nanoparticles, charged particles, charged ions, charged compound and combinations thereof from a mixture, wherein said method comprises the steps of carrying out an electrophoresis method or chromatographic method where a stationary phase comprising mechanically disintegrated nanofibrillar cellulose derived from plant material is used, wherein the stationary phase comprising nanofibrillar cellulose is in the form of a hydrogel.

6. The method according to claim 5 wherein the electrophoresis method is selected from gel electrophoresis, temperature gradient gel electrophoresis, denaturing gradient gel electrophoresis, two-dimensional gel electrophoresis and DNA gel electrophoresis.

7. The method according to claim 6 wherein the electrophoresis method comprises the steps of dispensing the mixture on or in the stationary phase, and applying an electrical field on the stationary phase whereby the components are separated.

8. The method according to claim 5 wherein the chromatographic method is selected from exclusion chromatography, ion exchange chromatography and affinity chromatography.

9. The method according to claim 8 wherein the chromatographic method comprises the steps of passing a mobile phase comprising at least one liquid through the stationary phase, where the mixture is dispersed in or on the stationary phase or it is mixed to the mobile phase, whereby the components are separated.

10. The method according to claim 9, wherein pressure or gravitational force is used.

11. The method of claim 1, further comprising forming the stationary phase from dry mechanically disintegrated nanofibrillar cellulose.

12. An electrophoresis kit for use in the method of claim 1, comprising stationary phase comprising mechanically disintegrated nanofibrillar cellulose derived from plant material, and reagents.

* * * * *